United States Patent [19]

Ditter et al.

[11] 4,026,993
[45] May 31, 1977

[54] SYNTHESIS OF DECABORANE-14 AND ALKYL-SUBSTITUTED DECABORANE-14

[75] Inventors: Jerome F. Ditter, Santa Ana; Eugene B. Klusmann, Irvine, both of Calif.

[73] Assignee: The United States of America as represented by the Secretary of the Navy, Washington, D.C.

[22] Filed: Aug. 23, 1976

[21] Appl. No.: 716,730

[52] U.S. Cl. .............................. 423/294; 423/295; 260/606.5 B

[51] Int. Cl.$^2$ ........................................ C01B 35/18

[58] Field of Search ........................... 423/294, 295; 260/606.5 B, DIG. 1

[56] References Cited

UNITED STATES PATENTS 3,152,867  10/1964  Tyson ................................. 423/294
3,383,399  5/1968  Stafiej et al. ............. 260/606.5 B X Primary Examiner—G. O. Peters
Attorney, Agent, or Firm—R. S. Sciascia; Philip Schneider; Thomas McDonnell

[57] ABSTRACT

A method for preparing a mixture of decaborane-14 and an alkyl-substituted decaborane-14 which comprises admixing an ethereal solution of nonaborane-14 ions with an alkaliboron halide at a temperature from 20° C to 30° C and at pressure from atmospheric pressure to 400 psig and a method of preparing decaborane-14 which comprises preparing an ethereal solution of nonaborane-14 by a reaction in an ethereal solution of an alkali metal borohydride with an excess of pentaborane-9 at temperature from 20° C to 30° C and admixing this ethereal solution of nonaborane-14 ions with diborane-6 at a temperature from 20° C to 30° C and at a pressure of at least 50 psig. Such compounds are useful as precursor compounds for the synthesis of important carborane derivatives, such as n-hexylcarborane (a catalyst for rocket propellants) and high-temperature-resistant carborane/siloxane polymers.

7 Claims, No Drawings

SYNTHESIS OF DECABORANE-14 AND ALKYL-SUBSTITUTED DECABORANE-14

BACKGROUND OF THE INVENTION

This invention relates generally to inorganic synthesis and more particularly to synthesis of decaborane-14 and derivatives.

Decaborane-14 as well as alkyl-substituted decaborane-14 is an important compound in the synthesis of certain carboranes and carborane/siloxane polymers. The only previously known synthesis of decaborane-14 is by the pyrolysis of $B_2H_6$ at temperatures near 180° C. The alkyl-substituted decaboranes in the past have been prepared through the reaction of decaborane-14 with electrophiles. The pyrolysis method has the disadvantage of producing low yields, while syntheses of alkylated decaboranes have the disadvantage of requiring decaborane as a starting material, which is a more expensive commodity than pentaborane-9.

SUMMARY OF THE INVENTION

It is therefore an object of this invention to provide a method for preparing both decaboranes and alkylated decaboranes.

Another object of this invention is to provide a method for preparing these compounds easily at room temperature from a less expensive starting material.

A further object of this invention is to provide a modification of the previous reaction which produces decaborane-14 with any alkyl substitution.

These and other objects are achieved through the formation of the $B_9H_{14}$ ion in an ethereal solution and the reaction thereof with a lower alkyl boronhalide or diborane-6 at room temperature.

DETAILED DESCRIPTION OF THE INVENTION

The ethereal solution of nonaborane-14 ions may be prepared by the method disclosed in Savoy, C.G. and Wallbridge, *The Reaction of Pentaborane (9) with Alkali Metal Hydroborates*, in *Inorganic Chemistry* 10:419 (1971) wherein pentaborane-9 and an alkali metal borohydride, e.g., sodium or potassium or lithium borohydride react in an ethereal solution to produce nonaborane-14 ions ($B_9H_{14}^-$). In the practice of this invention, potassium and lithium borohydrides may also be used. The ether may be monoglyme ether, diglyme ether, tetrahydrofuran, dimethyl ether, diethyl ether, and the like. Glyme ethers are preferred because of their low volatility and the ease with which products are separated therefrom. An ethereal solution of $B_9H_{14}^-$ ions may also be prepared by simply dissolving an alkali metal nonaborane-14 in an ether. This invention is not meant to be limited to any specific manner of preparing the required nonaborane-14 ions.

The dialkylborane halide may have an indeterminate number of carbon atoms in the alkyl group, and the halide may be either chloride or bromide. Preferably each of the alkyl groupsin the dialkylboronhalide contains from 1 to 5 carbon atoms so that the by-product alkane is sufficiently volatile to acilitate separation from the product mixture.

The most probable reactions occurring during this synthesis is illustrated for sodium nonaborane-14 and dimethylboronchloride as follows:

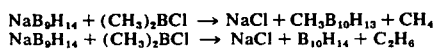

The driving force of each reaction presumably is derived from the formation of the salt and the volatile hydrocarbon. In carrying out this reaction the reactants may be mixed in any molar ration, but the preferred $B_9H_{14}^-$ to-halide ratio is 1:1, which is the stoichiometric ratio. An excess of either would produce no advantages but would constitute decreased yield. The amount of solvent is at least sufficient to dissolve both reactants and product. The two reactants may be introduced in any order into the reaction vessel.

To produce only decaborane-14, the ethereal solution of nonaborane-14 is prepared according to the Savoy and Wallbridge method, as was previously discussed herein with the modification of reacting the pentaborane-9 in an excess from 10 mole percent to 50 mole percent of the stoichiometric amount, with 20 to 40 mole percent in excess prefered. This solution is reacted with diborane-6 at a temperature from 20° C to 30° C. A possible mechanism for the preparation is:

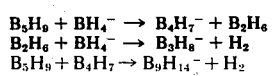

This is the initial nonaborane-14 (negative ion) reaction mixture. Overall, the reaction for this mixture is:

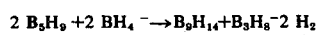

When excess $B_2H_6$ is added to this mixture, the probable sequence is:

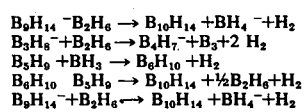

The complete overall reaction then is:

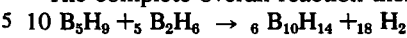

The following examples are given by way of illustratio and are not intended to limit the specification or the claims to follow in any manner.

Example I

SYNTHESIS OF $CH_3B_{10}H_{13}$ AND $B_{10}H_{10}$ from DIMETHYLBORONCHLORIDE AND $B_9H_{14}$ Thirty millilters of monoglyme was dried over $NaBH_4$ and was filtered. The dry monoglyme was added to 0.931g (0.0245 moles) of $NaBH_4$ to produce a saturated solution, and then 0.79g (0.0122 moles) of $B_5H_9$ was transferred in at -196° C. The mixture was allowed to warm slowly to room temperature (23° C) in 2 hours. Upon nearing room temperature the solid melted, and stirring with a magnetic stirrer became possible.

Approximately half of the liquid was removed by vacuum pumping, and the remaining solution was filtered in a dry box. Two milliltiers of the filtrate was taken, and $(CH_3)_2BCl$ was condensed thereon at -196° C. Again the mixture was warmed over a two-hour period to room temperature (23° C) at which temperature a rigorous reaction took place. During the reaction volatile products were evolved and were pumped off. Mass spectral analysis of the residue showed that $CH_3B_{10}H_{13}$ and $B_{10}H_{14}$ were formed.

Example II

The reactor was assembled from 1-inch diameter stainless steel tubing and had a 0–300 psi gauge attached. THe volume of the reactor, including the gauge, was determined to be 83 c.c.

A saturated monoglyme solution of $NaBH_4$ was prepared as in Example I. Five milliliters of this solution which would contain 0.006 moles of $NaBH_4$ was placed in the reactor. The reactor was then cooled to -196° C by contact with liquid nitrogen and was evacuated. Five milliliters (0.05 mol) of $B_5H_9$ and 0.044 moles of $B_2H_6$ were then transferred to the reactor. Upon warming to 23° C, the pressure was 20 psig. After the reactor had stood for 2 days at 23° C, the pressure was 260 psig due to the newly formed hydrogen. The reactor was allowed to stand for another three weeks. At the end of this period of time the pressure exceeded the maximum gauge reading. Hydrogen and other volatiles were driven off, and the residue was analysed by mass spectrometry. The results showed that a large yield of $B_{10}H_{14}$ was produced.

Obviously many modifications and variations of the present invention are possible in light of the above teachings. It is therefore to be understood that, within the scope of the appended claims, the invention may be practiced otherwise than as specifically described.

What is claimed and desired to be secured by letters patent of the United States is:

1. A method for preparing a mixture of decarborane-14 and alkyl-substituted dicarborane which comprises:
    admixing an ethereal solution of nonaborane-14 ions with an dialkylboronhalide, wherein said halide is selected from the group consisting of chloride and bromide, at a temperature from 20° C to 30° C.

2. The method of claim 1, wherein said ethereal solution results from admixing pentaborane-9 and an alkali metal borohydride selected from the class consisting of sodium borohydride, potassium borohydride, and lithium borohydride in an ether at a temperature from 20° C to 30° C 3. The method of claim 2, wherein said alkali borohydride is sodium borohydride and said temperature is from 22° C to 27° C.

4. The method of claim 1, wherein said alkaliboronhalide is an alkaliboronchloride.

5. The method of claim 4, wherein said alkali boronhalide is selected from the class consisting of methylboronchloride and ethylboronchloride, said temperature is from 22° C to 27° C, and said pressure is at least 14.7 psi.

6. A method for preparing decaborane-14 which comprises:
    preparing an ethereal solution of nonaborane by reacting pentaborane-9 with an alkali metal borohydride in a borane-to-borohydride mole ratio from 1.1:1.0 to 1.5:1.0 at temperature from 20° C to 30° C; and
    admixing said etheral solution with diborane-6 at temperature from 20° C to 30° C.

7. The method of claim 6, wherein borane-to-borohydride mole ratio is from 1.2:1.0 to 1.4:1.0 and said nonabborane reaction temperature is from 22° C to 27° C.

* * * * *